US006312955B1

(12) United States Patent
Hruby et al.

(10) Patent No.: US 6,312,955 B1
(45) Date of Patent: Nov. 6, 2001

(54) STREPTOCOCCUS GORDONII STRAINS RESISTANT TO FLUORODEOXYURIDINE

(75) Inventors: Dennis E. Hruby; Christine A. Franke, both of Albany, OR (US)

(73) Assignee: Siga Pharmaceuticals, New York, NY (US)

(*) Notice: Subject to any disclaimer, the term of this patent is extended or adjusted under 35 U.S.C. 154(b) by 0 days.

(21) Appl. No.: 09/301,456

(22) Filed: Apr. 29, 1999

(51) Int. Cl.$^7$ .................................................. C12N 15/01
(52) U.S. Cl. .................. 435/441; 424/50; 424/93.44; 424/244.1; 435/7.34; 435/29; 435/244; 435/245; 536/23.1
(58) Field of Search ............................... 424/50, 93.44, 424/164.1, 184.1, 234.1, 802, 244.1; 435/7.34, 69.1, 29, 170, 252.3, 441, 244; 530/350; 536/23.1

(56) References Cited

FOREIGN PATENT DOCUMENTS

WO9640943    12/1996   (WO).

OTHER PUBLICATIONS

Lehninger et al. Principals of Biochemistry. (1993) Worth Publishers Inc. pp. 715.*
Knox et al. Isoloation and characterization of mutants of mesophilic methonogenic bacteria resisitant to analogues of DNA bases and nucleosides. Archives of Microbiology. vol. 149 (1988) pp. 557–560.*
Franke et al., "Streptococcus gordonii Strains Resistant to Fluorodeoxyuridine Contain Mutations in the Thymidine Kinase Gene and are Deficient in Thymidine Kinase Activity", Antimicrobial Agents and Chemotherapy, vol. 44, No. 3, Mar. 2000, pp. 787–789 XP002154467.
Darland et al, "Isolation of a thymidine Kinase Negative Mutant of a Nocardia Lactamdurans", Fems Microbiology Letters, vol. 65, pp. 229–232 (1989) XP000926057.
Mandelbaum–Shavit et al, "Mechanism of Resistance of Pediococcus Cerevisiae Strains to 5–Fluorodeoxyuridine" Biochimica et Biophysica Acta vol. 543, pp. 1–9 (1978) XP000926054.
Bean et al, "5–Fluoropyrimidine–Resistant Mutants of Pneumococcus" Journal of Bacteriology, vol. 113, No. 3, pp. 1348–1355 (Mar. 1973) XP000926065.
Palu et al, "A Point Mutation in the Thymidine Kinase Gene is Responsible for Acyclovir–Resistance in Herpes Simplex Virus Type 2 Sequential Isolates", Virus Research, vol. 25, pp. 133–144(1992) XP000926071.
Hruby, "Vaccinia Virus: A Novel Approach for Molecular Engineering of Peptide Vaccines", Seminars in Hematology, vol. 30, No. 4, pp. 35–44 (Oct. 1993), XP000926093.
J. Martinussen et al, "Cloning and Characterization of upp, a Gene Encoding Uracil Phosphoriboxyltransferase from Lactococcus Lactis" Journal of Bacteriology, Nov. 1994, p. 6457–6433, vol. 176, No. 21.

Beck et al., "Metabolism of Pyrimidines and Pyrimidine Nucleosides by Salmonella typhimurium", Journal of Bacteriology, vol. 110, No. 1, pp. 219–228 (1972).
Black et al. "Nucleotide Sequence of the Escherichia coli Thymidine Kinase Gene Provides Evidence for Conservation of Functional Domains and Quaternary Structure", Molecular Microbiology vol. 5, No. 2, pp. 373–379 (1991).
Drinkwater et al., "Chemically Induced Mutagenesis in a Shuttle Vector With a Low–background Mutant Frequency", Proc. Natl. Acad. Sci. USA vol. 83, pp. 3402–3406 (1986).
Bollet et al., "A Simple Method for the Isolation of Chromosomal DNA from Gram Positive or Acid–fast Bacteria" Nucleic Acids Research, vol. 19, No. 8, p. 1955 (1991).
Black et al., "Site–directed Mutagenesis of a Conserved Domain in Vaccinia Virus Thymidine Kinase" Journal of Biological Chemistry vol. 267, No. 10, pp. 6801–6806 (1992).
Dube et al., "The Association of Thymidine Kinase Activity and Thymidine Transport in Escherichia coli" Gene vol. 99, pp. 25–29 (1991).
Fischetti et al., "Expression of Foreign Proteins on Gram–Postive Commensal Bacteria for Musocal Vaccine Delivery" Curr. Opinions in Biotechnology vol. 4, pp. 603–610 (1993).
Frandsen et al., "Ecology of Viridans Streptococci in the Oral Cavity and Pharynx" Oral Microbiol Immunol. vol. 6, pp. 129–133 (1991).
Hiraga et al., A Deoxythymidine Kinase–Deficient Mutant of Escherichia Coli, Biochimica et Biophysica Acta vol. 145 pp. 41–51 (1967).
Hruby et al., "Control of Expression of the Vaccinia Virus Thymidine Kinase Gene", Journal of Virology, vol. 40, No. 2, pp. 456–464 (1981).
Hruby et al., "Mapping and Identification of the Vaccinia Virus Thymidine kinase Gene", Journal of Virology vol. 43, No. 2, pp. 403–409 (1982).
Igarashi et al., "A Deoxythymidine Kinase Deficient Mutant of Escherichia Coli II. Mapping and Transduction Studies with Phage Φ80" Genetics vol. 57, pp. 643–654 (1967).

(List continued on next page.)

Primary Examiner—Jeffrey Stucker
Assistant Examiner—Ulrike Winkler
(74) Attorney, Agent, or Firm—Burns, Doane, Swecker & Mathis, L.L.P.

(57) ABSTRACT

The present invention features gram-positive bacteria resistant to 5-fluorodeoxyuridine (FUdR). Such bacteria will preferably be commensal, and will not be resistant to antibiotics. Bacteria according to the present invention may also be transformed with DNA encoding an antigenic protein. Such transformed bacteria may be used to formulate a vaccine, in order to stimulate an immune response to the antigenic protein in a patient. The present invention further provides a method for isolating gram-positive bacteria resistant to FUdR.

13 Claims, 5 Drawing Sheets

OTHER PUBLICATIONS

McNab, R., "Cloning and Sequence Analysis of Thymidine Kinase from the Oral Bacterium *Streptoccus gordonii*" *FEMS Microbiology Letters* vol. 135, pp. 103–110 (1996).

Medaglini, D. et al. "Mucosal and Systemic Immune Responses to a Recombinant Protein Expressed on the Surface of the Oral Commensal Bacterium *Streptococcus gordonii* After Oral Colonization" *Proc. Natl. Acad. Sci. USA* vol. 92, pp. 6868–6872 (1995).

Pozzi, G. et al. "Host–Vector System for Integration of Recombinant DNA into Chromosomes of Transformable and Nontransformable Streptococci" *J Bacteriology*, pp. 1969–1972 (1988).

Summers, W. C. et al. "A Method for Selection of Mutations at the *tdk* Locus in *Escherichia coli*" *Journal of Bacteriology* vol. 175, No. 18 pp. 6049–6051 (1993).

* cited by examiner

SEQUENCE LISTING

<160> NUMBER OF SEQ ID NOS: 4

<210> SEQ ID NO 1
<211> LENGTH: 30
<212> TYPE: DNA
<213> ORGANISM: Streptococcus gordonii

<400> SEQUENCE: 1
gattatggct caattatatt ataaatacgg                                    30

<210> SEQ ID NO 2
<211> LENGTH: 29
<212> TYPE: DNA
<213> ORGANISM: Streptococcus gordonii

<400> SEQUENCE: 2
caattattaa tgtctggctt aaaataatg                                     29

<210> SEQ ID NO 3
<211> LENGTH: 20
<212> TYPE: DNA
<213> ORGANISM: Streptococcus gordonii -continued

```
<400> SEQUENCE: 3
taatacgact cactataggg                                              20

<210> SEQ ID NO 4
<211> LENGTH: 18
<212> TYPE: DNA
<213> ORGANISM: Streptococcus gordonii

<400> SEQUENCE: 4
caggaaacag ctatgacc                                                18
```

STREPTOCOCCUS GORDONII STRAINS RESISTANT TO FLUORODEOXYURIDINE

BACKGROUND OF THE INVENTION

1. Field of the Invention

The present invention relates to gram-positive bacterial strains resistant to 5-fluorodeoxyuridine, and to methods of producing such bacterial strains.

2. Description of the Related Art

Commensal Gram-positive bacteria are currently being developed as live vaccine vectors able to colonize mucosal surfaces and stimulate a secretory IgA, as well as a systemic immune, response to a recombinant antigen displayed on the surface of these organisms. One such promising live vaccine delivery system candidate is the oral bacterium *Streptococcus gordonii*, a component of human dental plaque which is able to colonize most oral sites. One important issue related to the utilization of these organisms as live vaccine vectors is the need to develop non-antibiotic selectable markers to employ during the manipulation of these recombinant organisms in the research and clinical laboratories, as well as to monitor colonization in animal studies and possible dispersal of these organisms in the environment.

Thymidine kinase (TK; EC 2.7.1.21) is a key enzyme in the salvage pathway of pyrimidine nucleotide metabolism which catalyzes the formation of thymidylate from thymidine and ATP. Previous studies in both *Escherichia coli* and *Salmonella typhimurium* have suggested it is possible to select for tdk mutations in essentially any genetic background on the basis of their resistance to the pyrimidine analog fluorodeoxyuridine. Presumably, when FUDR is phosphorylated by TK to 5-fluorodeoxyuridine monophosphate it inhibits thymidylate synthetase, the final enzyme in the de novo synthetic pathway to thymidylate synthesis. The resultant absence of a source of preformed thymidine will deplete the cell of the essential metabolite TMP and thus, the selection pressure for the mutation of tdk. Indeed, previous isolates of *Escherichia coli*, resistant to FUDR, all possessed mutations that mapped to a single locus at 27.5 minutes on the *E. coli* genetic map and were deficient in thymidine kinase activity. This suggests that the usual mechanism for FUdR-resistance is the loss of thymidine kinase activity and that all mutations in FUdR$^r$ mutants of *E. coli* occur at the tdk locus.

Since the gene encoding thymidine kinase of *S. gordonii* has been cloned and the nucleotide sequence determined, we sought to determine if the selection for FUdR-resistant strains of *S. gordonii* was possible and, if so, to evaluate it as a dominant selectable marker.

SUMMARY OF THE INVENTION

Briefly, the present invention features gram-positive bacteria resistant to 5-fluorodeoxyuridine (FUdR). Such bacteria will preferably be commensal, and will not be resistant to antibiotics. Bacteria according to the present invention may also be transformed with DNA encoding an antigenic protein. Such transformed bacteria may be used to formulate a vaccine, in order to stimulate an immune response to the antigenic protein in a patient.

The present invention further provides a method for isolating gram-positive bacteria resistant to FUdR.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 1. tdk Gene Structure of FUdR$^r$ mutants. Diagrammatic representations of major features of open reading frames deduced from the nucleotide sequence analysis of the tdk gene from the indicated strains are provided. The position and identity of predicted start and stop codons are shown with the codon number indicated by the subscript number. For the FUdR$^r$ mutants the identity of the original nucleotide and the mutation are shown. On the left are the strain designations and on the right are the predicted molecular weights of the polypeptides encoded by each of the tdk genes.

FIG. 2. Structural and functional analysis of FUdR$^r$ tdk genes. Transcripts of the tdk genes of wild-type *S. gordonii* and the FUdR$^r$ mutants were prepared, and then translated in rabbit reticulocyte lysates in the presence or absence of [$^{35}$S]methionine. A) The radiolabeled translation products were resolved by electrophoresis on 12% polyacrylamide gels containing SDS and visualized by autoradiography. Lane M, molecular weight markers (46, 30, 21.5, 14.3, 6.5 and 3.4 kDa, respectively); Lane 1, no RNA added; Lane 2, GP204; Lane 3, SP204(1-1); Lane 4, SP204(1-2); Lane 5, SP204(10-1). B) The unlabeled translation products were tested for thymidine kinase enzyme activity using a previously described protocol which measures the conversion of [$^3$H] thymidine to [$^3$H] thymidine monophosphate. The incorporation of the radiolabel is shown for each of the tdk gene products. The lane designated "None" represents the incorporation directed by a reticulocyte lysate to which no exogenous RNA had been added.

Replicate BHI broth cultures were inoculated with equivalent amounts of GP204 (open circles) or SP204 (closed circles). Cultures were incubated at 37° C. with no agitation. Samples were removed every 30 minutes are the absorbance at 590 nm determined.

Broth cultures of GP204 and SP204(1-1) were grown to mid-log. The absorbance of the culture at 590 nm was determined. A one ml aliquot of each culture was removed, mixed with [$^3$H] thymidine, and incubated at 37° C. Triplicate 50 pi samples were removed from each aliquot after 0 and 10 minutes incubation and processed to determine TCA-precipitable radioactivity. The incorporated counts obtained were then normalized to the number of bacterial cells.

FIG. 5. Mouse colonization by GP204 and SP204(1-1). Broth cultures of GP204 and SP204(1-1) were grown to mid-log phase. Cells were harvested and washed once with broth. The cell pellets were resuspended in broth to obtain a concentration such that 10$^9$ bacteria were contained in 50 pi which was instilled intransally and orally into 10 female BALB/c mice per group on each of two days (48 hours apart). The oral cavities of the inoculated mice were swabbed weekly and plated onto blood agar plates containing streptomycin. If >2 colonies of streptomycin-resistant, α-hemolytic gram-positive cocci were recovered the mouse was scored as positive for colonization, as indicated by a filled circle.

DETAILED DESCRIPTION OF THE PREFERRED EMBODIMENTS OF THE INVENTION

More particularly, the present invention relates to a method for isolating a strain of gram-positive bacteria resistant to 5-fluorodeoxyuridine ("FUdR") comprising (1) culturing the bacteria on culture medium containing FUdR; and (2) selecting those bacteria that grow in the presence of FUdR.

The culture medium for use in the method of the present invention is preferably selected from the group consisting of brain-heart infusion and tryptic soy broth. The culture medium for use in the method of the present invention may comprise from about 0.5 to about 50 µg/ml FUdR. In a preferred embodiment, the culture medium for use in the method of the present invention comprises from about 1 to about 10 µg/ml FUdR. The culture medium preferably further comprises about 12.5 µg/ml uridine and about 2 µg/ml thymidine.

Any gram-positive bacteria may be used in the method of the present invention. Preferably, the bacteria used in the present invention are gram-positive commensal bacteria, and are not resistant to antibiotics. A particularly preferred species of bacteria for use in the present invention is *Streptococcus gordonii*.

The present invention further provides isolated gram-positive bacteria resistant to FUdR. Such bacteria may be isolated by the method of the present invention, or may be produced by recombinant means. Preferably, bacteria according to the present invention will be commensal bacteria, such as *Streptococcus gordonii*, and will not be resistant to antibiotics.

A bacterium according to the present invention will be resistant to FUdR due to a point mutation in the tdk gene that results in the introduction of a translational termination codon in the tdk ORF. Such a mutation results in the expression of a prematurely terminated TK polypeptide. In a preferred embodiment of the present invention, said prematurely terminated TK polypeptide lacks domain VII.

FUdR-resistant bacteria according to the present invention may be further transformed with DNA encoding antigenic proteins in order to stimulate an immune response in a patient. In a preferred embodiment, bacteria according to the present invention for use in vaccine compositions will be transformed with DNA encoding a surface protein of a disease-causing bacteria, in order to stimulate an immune response to that disease in a patient. As used in the context of the present invention, the term "patient" will be understood to refer to any animal, including but not limited to humans, in which an immune response is desired to be generated. In a particularly preferred embodiment of the present invention, the DNA will encode the streptococcal M6 protein, or a fragment thereof, as described in U.S. Pat. Nos. 4,784,948 and 5,840,314, the contents of which are incorporated herein by reference. Gram-positive bacteria may be transformed to express heterologous proteins on their surface using the methods described, for example, in U.S. Pat. Nos. 5,616,686, 5,786,205, and 5,821,088, the contents of which are incorporated herein by reference.

The following examples are presented in order to more fully illustrate the preferred embodiments of the invention. They should in no way be construed, however, as limiting the broad scope of the invention.

EXAMPLE 1

This study describes the selection of FUdR$^r$ strains of *S. gordonii* and the characterization of their genetic, biochemical and growth (in vitro and in vivo) properties. We demonstrate that spontaneous FUdR-resistant strains of *S. gordonii* are readily selected in a single-step, identify the nature of the resultant mutations in the tdk locus and assay the biochemical consequences of these mutations on thymidine kinase enzyme activity and thymidine incorporation. Additionally, we show that colonization of mice inoculated with an oral/intranasal inoculum of a FUdR-resistant strain was comparable to parental *S. gordonii*.

Experimental Procedures

Bacterial Strains and Culture Conditions

*Streptococcus gordonii* strain GP204, a spontaneous streptomycin resistant mutant of *Streptococcus gordonii* strain V288 (ATCC 35105), is the parental strain from which the FudR$^r$ *S. gordonii* strains described in this study were selected. *S. gordonii* cultures were grown as static cultures at 37° C. in either brain heart infusion broth (BHI; DIFCO) or tryptic soy broth (DIFCO) supplemented with the appropriate constituents as indicated in the text (streptomycin sulfate, 500 µg/ml; FUdR, 50 µg/ml, 12.5 µg/ml uridine and 2 µg/ml thymidine). *E. coli* strain KY895 (F-, tdk-, 1-ilv) is deficient in thymidine kinase activity. *E. coli* strain KY895 containing a plasmid expressing the *E. coli* tdk gene which restores TK activity was also utilized in this study PCR amplification and Nucleotide Sequence Analysis of tdk Genes The polymerase chain reaction (PCR) was employed to amplify the thymidine kinase open reading frame from chromosomal DNA preparations of *S. gordonii* strains. The methods employed were an adaptation of those prescribed by the manufacturers of the Gene Amp XL PCR Kit (Perkin Elmer) and the Tth Start Antibody (Clontech). Briefly, PCR reactions were 50 µl reactions containing the following components: (XL Buffer II (1×), Mg(OAc)$_2$ Solution (1.1 mM), Primer CF12 (SEQ. ID NO: 1) (5'-GATTATGGCTCMTTATATTATAAATACGG-3', 0.4 µM), Primer CF13 (SEQ. ID NO: 2) (5'-CAATTATTMTGTCTGGCTTAAAATAATG-3', 0.4 µM), dNTPs (0.2 µM), Tth Start Antibody (0.88 µg), rTth DNA polymerase (2 U), SP204(1-1) Lot #SP22-09 chromosomal DNA (180 ng) or GP204 Lot #SP5-IB chromosomal DNA (262 ng)). The Tth Start Antibody and rtth DNA polymerase were prepared as a 56:1 molar solution (Tth Start Antibody: rTth DNA polymerase) and incubated for 5 minutes at room temperature prior to addition to the PCR reaction. The reactions were layered with silicon oil and then subjected to thermal cycling in an ERICOMP Twin Block thermal cycler according to the following program: ((94° C., 1 min; 53° C., 1 min; 72° C., 2 min) 1×; (94° C., 30 sec; 55° C., 1 min; 72° C., 1 min) 35× and (72° C., 10 min) 1×). The 576 bp PCR products were cloned into the pCR2.1 vector supplied in the Invitrogen TA Cloning Kit according to the instructions prescribed by the manufacturer.

Plasmid DNA template was prepared using QIAGEN QIAprep Spin Miniprep Kit and quantitated by fluorometer (Hoeffer DYNA Quant 200) using calf thymus DNA as the calibration standard. The plasmid DNA templates were submitted to the Central Services Laboratory of the Center for Gene Research and Biotechnology, Oregon State University for DNA sequence determination. The DNA dideoxy chain termination sequencing reactions were prepared using the ABI Prism™ Dye Primer Cycle Sequencing Core Kit with AmpliTaq® DNA Polymerase, FS Kit according to the method prescribed by the manufacturer (PE Applied Biosystems P/N 402114, Revision C). Both templates were sequenced using the T7 dye primer (SEQ. ID NO: 3) (5'-TAATACGACTCACTATAGGG-3') and the M13 Reverse dye primer (SEQ. ID NO: 4) (5'-CAGGAAACAGCTATGACC-3') and the sequencing reactions were analyzed on an ABI 373 sequencer.

Cell-free Transcription and Translation

Coupled transcription/translation reactions were performed concurrently in the absence of radiolabel and in the presence of L-[$^{35}$S]-methionine (Amersham Radiochemicals Co.; 1249 Ci/mmol) using plasmid DNA templates to program the TnT Reticulocyte Lysate kit (Promega) according to the manufacturer's directions. Radioactive polypeptides synthesized were analyzed by SDS-polyacrylamide gel electrophoresis and visualized by autoradiography.

Thymidine Kinase Enzyme Assay and Thymidine Incorporation

Thymidine kinase activity of nonradiolabeled in vitro translation products was determined by a filter-binding assay that follows the conversion of [$^3$H]-thymidine to [$^3$H]-TMP as described previously. Thymidine incorporation was measured on log phase cultures of S. gordonii strains. Aliquots from overnight cultures were diluted 1:100 with BHI broth containing 500 μg/ml of streptomycin sulfate and grown at 37° C. to an $A_{590nm}$=0.5. [$^3$H]dT (0.75 μM final concentration; 85 Ci/mmol) was added in a total volume of 1 ml and incubated at 37° C. After incubation, 50 μl aliquots were removed and spotted onto Whatman 3 MM filter paper discs previously wetted with 10% trichloroacetic acid (TCA) and processed to determine radiolabel incorporated as described previously.

Mouse Colonization

S. gordonii strains were grown in 50 mL cultures of BHI broth (with appropriate selective additives) at 37° C. to an $OD_{650}$≈0.8. 45 mL of this culture was centrifuged at 2,200×g for 20 min at 4° C. The supernatant was aspirated and the streptococcal cell pellet was resuspended in 1 mL of fresh BHI. This concentration of cell suspension delivered 1–5× $10^9$ cfu/50 μL dose. Colony counts were confirmed by plating of serial dilutions of the inoculum on 5% sheep blood agar containing appropriate selective additives. Female BALB/c mice (6–8 weeks; Charles River) were given streptomycin (5 gm/L) in their water, ad libitum, for 2 days prior to implantation of the S. gordonii (day −2), maintained on streptomycin water throughout the implantation process, and then returned to unsupplemented water thereafter. Mice were implanted with 50 μL of each cell suspension equally distributed between the nares and the oral cavity on Day 0 and the process was repeated with freshly grown cells on Day 2. The pharyngeal area, gums and teeth of each mouse were monitored for streptococcal colonization by using microswabs (Fisher) at weekly or biweekly intervals, with subsequent plating on 5% sheep blood agar containing appropriate selective additives. The plates were incubated at 37° C. for 48 hr before counting the resultant colonies.

Results

Selection of FUdR$^r$ Streptococcus gordonii Strains

Previous research in gram-negative bacterial systems has demonstrated that exposure of bacteria to inhibitory concentrations of 5-fluorodeoxyuridine (FUdR) results in the mutation and concomitant genetic inactivation of the bacterial genomic tdk gene. It was not known if gram-positive bacteria such as Streptococcus gordonii would behave similarly. To determine the relative FUdR-sensitivity of a representative gram-positive commensal bacterium, S. gordonii, strain GP204 (streptomycin-resistant, Sm$^r$) was plated onto FUdR selective plates. The selective plates were a brain heart infusion (BHI) agar base containing 1–60 μg/ml of FUdR in the presence of uridine (12.5 μg/ml) and thymidine (2 μg/ml), to facilitate the alternative de novo biosynthetic pathway of thymidylate synthesis. As positive and negative controls, respectively, we utilized an E. coli strain expressing a wild-type tdk gene and a well-studied TK$^-$ mutant (KY895). The results obtained indicated that the S. gordonii GP204 was remarkably sensitive to FUdR inhibition relative to E. coli. Whereas the TK$^+$ E. coli would form colonies in the presence of 60 μg/ml FUdR, marked inhibition of S. gordonii GP204 was evident in the presence of as little as 0.5 μg/ml FUdR. Therefore, to attempt the selection and isolation of FUdR S. gordonii strains, S. gordonii GP204 was plated onto replicate selective plates containing 1–10 μg/ml FUdR. Under these conditions, two FUdR$^r$ colonies were obtained on the plates containing 1μg/ml FUdR and were designated SP204(1-1) and SP204(1-2). One FUdR$^r$ colony grew out on the plates containing 10 μg/ml FUdR and was designated SP204(10-1). The Sm$^r$ phenotype of SP204(1-1), SP204(1-2) and SP204(10-1) was verified to ensure the strains were derived from parental strain S. gordonii GP204. Additional quantitative analyses revealed that the spontaneous mutation rate for producing S. gordonii GP204 FUdR-resistant mutants was 1×10$^{-6}$.

Nucleotide Sequence Analysis of the tdk loci of S. gordonii FUdR$^r$ Mutants

To determine if, as in the case of the gram-negative bacteria, the mutation responsible for the acquisition of FUdR resistance mapped to the tdk gene, the polymerase chain reaction (PCR) was employed to amplify the thymidine kinase open reading frame from chromosomal DNA preparations of S. gordonii strains SP204(1-1), SP204(1-2), SP204(10-1) and GP204 (included as a positive control for the PCR reaction). PCR primers were based on the previously published sequence of the S. gordonii tdk gene from strain DL-1 (Challis) and were designed to amplify a 579 base-pair (bp) DNA product encompassing the entire tdk locus (576 bp). In each case, unique PCR products of approximately 600 bp in size, as measured relative to DNA size standards, were obtained.

The amplified PCR products were excised from the agarose gel, ligated into the plasmid vector pCR2.1, and transformed into competent INVαF cells. Colonies resistant to ampicillin (50 μg/ml) were selected on agar plates. Plasmid DNA was prepared from representative colonies digested by restriction endonuclease EcoRI, and analyzed by agarose gel electophoresis to verify the presence of inserts of the appropriate size (~600 bp). The plasmid DNA from representative clones was sequenced on both strands utilizing the M13 reverse and T7 sequencing primers.

Figure 1:
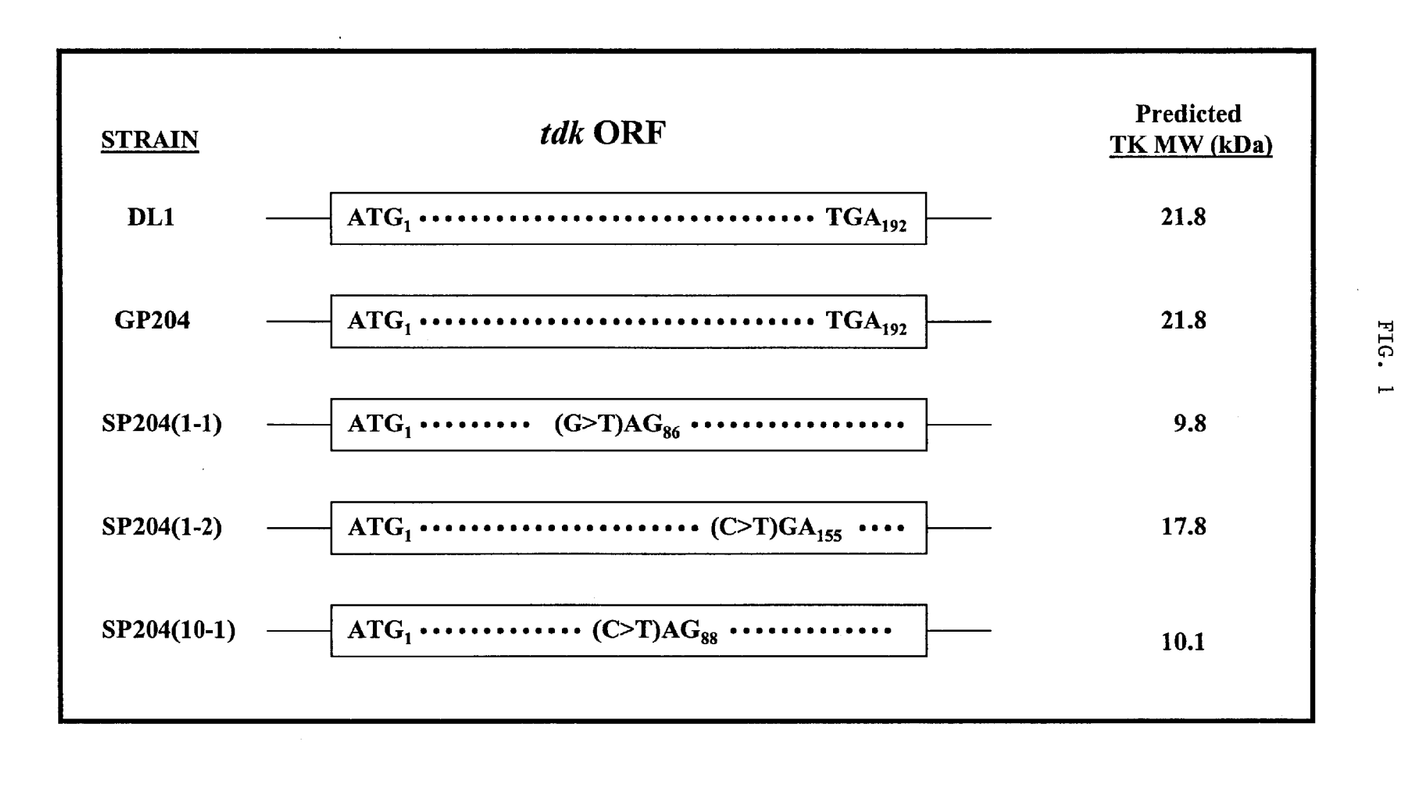

Analysis of the DNA sequence from the FUdR$^r$ strains revealed that the tdk ORFs each contained a single base-pair substitution, relative to the sequence of S. gordonii GP204, which resulted in the introduction of a translational termination codon in the tdk ORF at a unique position in each strain (FIG. 1). The tdk ORF for SP204(1-1) contained a GAG to TAG transversion mutation at codon 86 of the 191 amino acid tdk ORF. The mutation of SP204(1-2) was a CGA to TGA transition mutation occuring at codon 155. Another transition mutation of CAG to TAG at codon 88 of the tdk ORF was observed in SP204(10-1). It should also be noted that the derived nucleotide sequence of S. gordonii GP204 differed from that published for DLI (Challis) at a single residue, containing a silent A to G mutation at nucleotide 54 of the tdk ORF. SP204(1-2), SP204(10-1) also each contained the silent mutation at nucleotide 54 confirming their derivation from the parental strain S. gordonii GP204.

Loss of TK Activity in S. gordonii FUdRr Mutants

Figure 2:
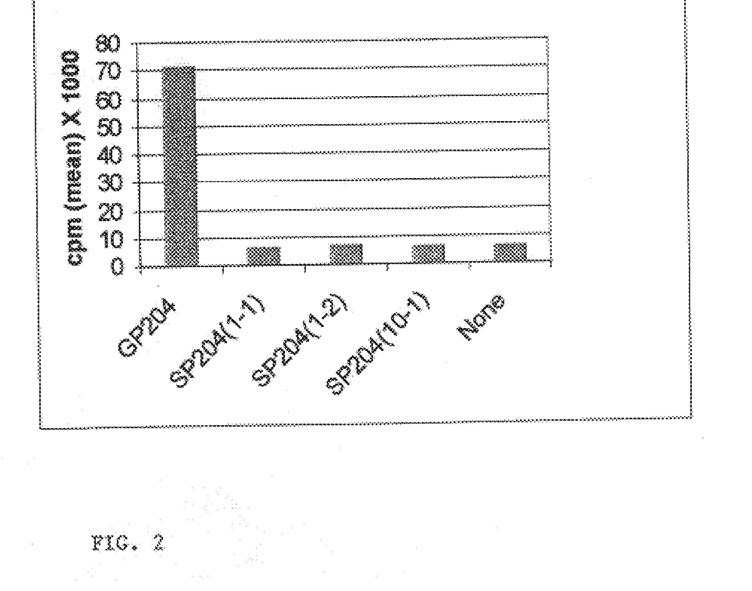

The predicted molecular mass of the full-length S. gordonii TK polypeptide is 21,843 daltons. The predicted molecular masses of the prematurely terminated TK polypeptides encoded by the SP204(1-1), SP204(1-2), SP204(10-1) FUdR$^r$ mutants are 9,800 daltons, 17,800 daltons and 10,100 daltons, respectively (FIG. 1). To verify these phenotypes, the FUdR$^r$ tdk loci cloned in the pCR2.1 plasmid vector were transcribed using T7 RNA polymerase, the derived transcripts translated in rabbit reticulocyte lysates in the presence of [$^{35}$S]methionine and the radiolabeled translation products analyzed by gel electrophoresis. The data in FIG. 2a shows that the apparent molecular masses of the labeled in vitro translation products observed in the fluorogram of this gel are in good agreement with the predicted sizes of the TK truncation products of the tdk loci of SP204(1-1), SP204(1-2), SP204(10-1), although the SP204(1-1) tdk-derived transcript was either poorly translated or the translation product was labile.

Previously, we have identified seven functional domains (I–VII) that are highly conserved in both eukaryotic and prokaryotic TK enzymes. The truncated TK enzymes encoded by SP204(1-1) and SP204(10-1) would lack domains III–VII whereas the truncated SP204(1-2) TK enzyme would lack essential domain VII, a four amino acid sequence near the carboxyl terminus. This observation would predict that none of the truncated FUdR$^r$ tdk ORFs would encode an active TK enzyme. To test this prediction, unlabeled translation reactions programmed with FUdR$^r$ tdk-derived in vitro transcription products were tested for thymidine kinase activity, as measured by the ability of the extracts to convert [$^3$H]thymidine to [$^3$H]TMP. As is evident in FIG. 2b, no [$^3$H]thymidine phosphorylating activity was present above background in the SP204(1-1), SP204(1-2), SP204(10-1) TK translations, whereas a high level of thymidine kinase activity was evident in the parental GP204 TK translation reaction. Taken together these data demonstrate that each FUdR$^r$ SP204 strain has a mutation within the tdk locus at the first base of a triplet codon which results in the introduction of a translational termination codon at a unique position in each strain. Analysis of in vitro translation products of the tdk ORF of each SP204 strain confirms that a truncated TK polypeptide is synthesized and that these incomplete polypeptides are thymidine kinase deficient.

In Vivo Consequences of FUdR$^r$ in S. gordonii

Having isolated and characterized FUdR$^r$ S. gordonii mutants, it was of interest to determine what, if any consequences the thymidine kinase deficient phenotype would have on the growth of S. gordonii cells in culture or in recipient animals. This information will be of importance if FUdR$^r$ is to be used instead of traditional antibiotic resistance as a selectable marker for the construction of recombinant S. gordonii strains and their implementation as vaccine delivery vehicles in vivo. Since all three of the FUdR$^r$ mutants (SP204(1-1), SP204(1-2), SP204(10-1)) exhibited the same TK$^-$ phenotype we selected one SP204(1-1) for further analysis to simplify the in vivo analyses.

Figure 3:
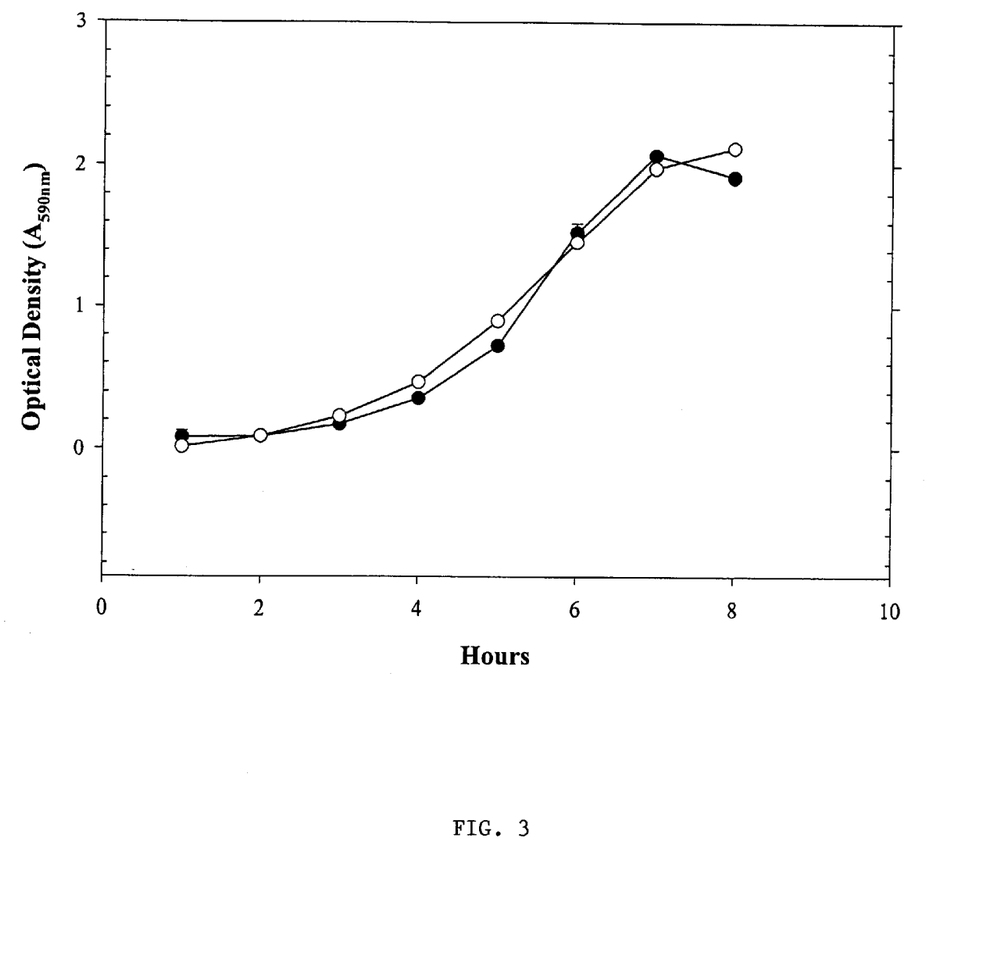
FIG. 3. Relative growth rates of GP204 and SP204(1-1) in BHI broth.

The first question to be addressed was whether the growth of SP204(1-1) was compromised under standard laboratory growth conditions. This question had already been partially answered by the ability to isolate and propagate the mutants on BHI plates, albeit in the presence of exogenously added uridine and thymidine. We addressed the issue more rigorously in broth cultures using a variety of culture media. What was found was that in minimal medium, such as trypticase soy broth (TSB), the growth of SP204(1-1) was severely inhibited relative to that of the parental strain GP204. This inhibition could be mostly, but not entirely, overcome by the addition of 50 µg/ml exogenous uracil to the growth medium (data not shown). In contrast, as shown in FIG. 3, SP204(1-1) grew quite well in rich broth culture (BHI). This experiment shows the result of inoculating a 1:100 back dilution of overnight cultures of GP204 and SP204(1-1) into fresh BHI broth, with no nucleotide supplements, and monitoring growth at 37° C. It can be seen that SP204(1-1) grows at the same rate and reaches the same cell density as does GP204 under these conditions, suggesting that any required exogenous nucleotides are supplied in the BHI formulation. This result supports the hypothesis that the FUdR$^r$ can be used as a selectable marker under culture conditions, but attention to the culture medium used is essential.

Figure 4:
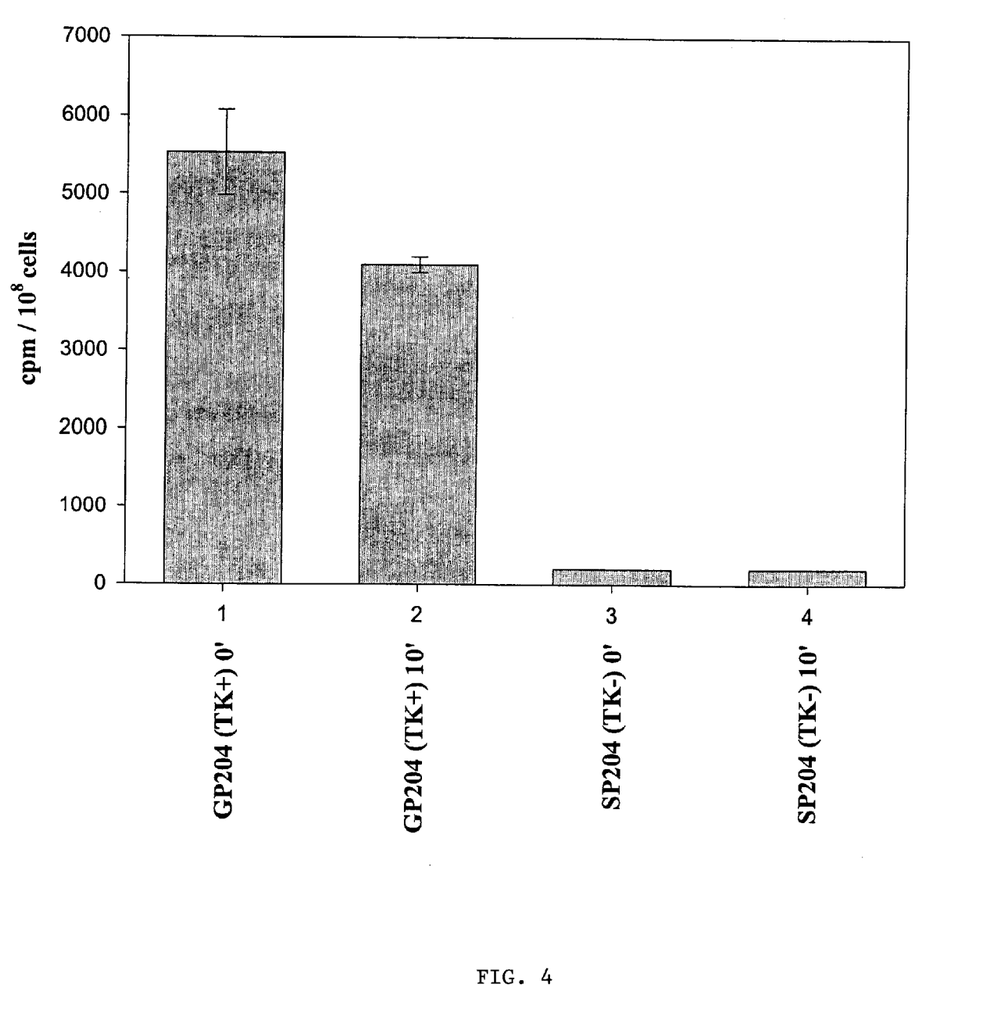
FIG. 4. Uptake and incorporation of thymidine by GP204 and SP204(1-1).

The next question to be addressed was what effect, if any, the presence of the FUdR$^r$ marker would have on nucleoside uptake and/or metabolism. Previous work in the gram-negative bacterium E. coli has suggested that there is an intrinsic link between thymidine uptake and the level of intracellular thymidine kinase activity. To determine if gram-positive bacteria such as S. gordonii react in the same manner, thymidine uptake was directly measured in GP204 and SP204(1-1). [$^3$H]thymidine was added to duplicate one ml aliquots of log phase cultures of GP204 and SP204(1-1). After 0 or 10 minutes incubation the cells were precipitated with TCA, washed and counted to determine intracellular radioactivity. As the data in FIG. 4 demonstrates, whereas GP204 was able to rapidly assimilate thymidine, SP204(1-1) was greatly inhibited, accumulating only trace amounts of radioactivity after even ten minutes of incubation. This result suggests a commonality in the manner by which nucleotide uptake and metabolism is linked in gram-negative and gram-positive bacteria, and raises the issue of whether the growth of a TK7 strain might be compromised in an in vivo situation where the concentration or exogenous nucleosides/nucleotides is unknown.

Figure 5:
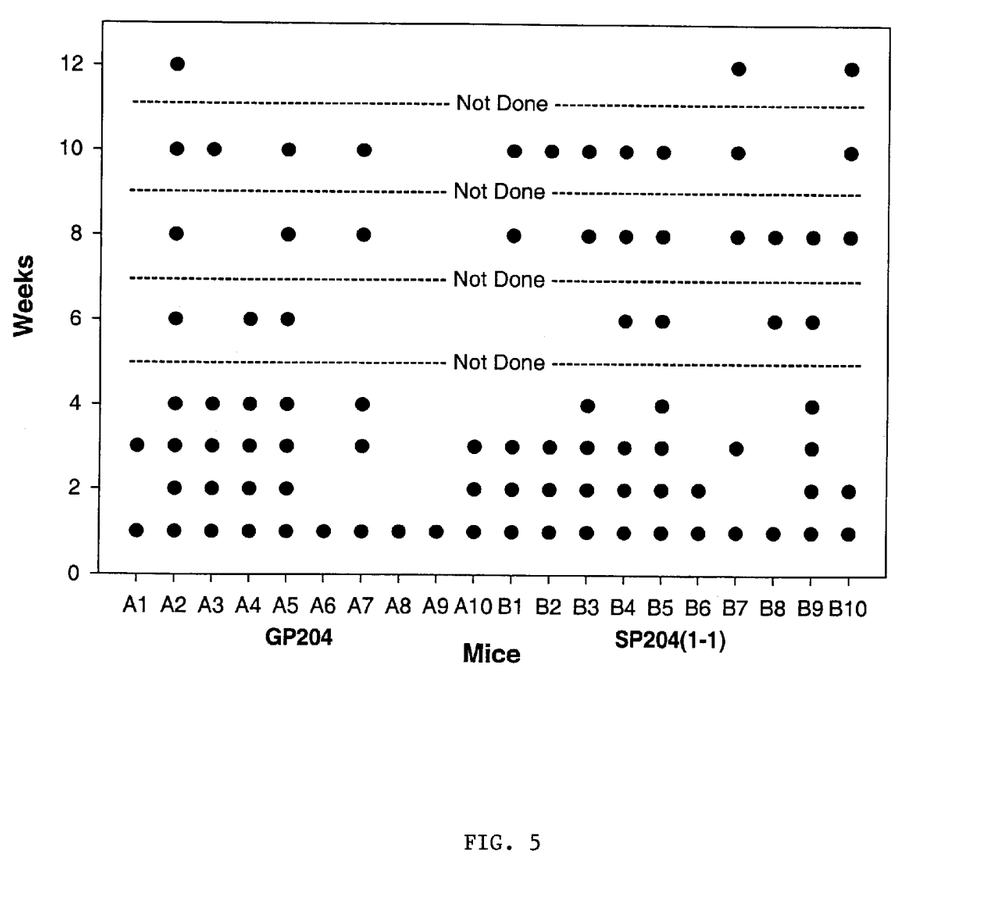

Since both growth and thymidine uptake by SP204(1-1) appeared to be compromised in vitro, at least under some culture conditions, it was of interest to determine if the ability of SP204(1-1) to colonize and persist in recipient animals, where the nutritional conditions are variable and unknown, was similarly affected. If so, then use of the FUdR$^r$ marker would be contraindicated in potential vaccine formulations. As a model system we chose the BALB/c mouse. Previous work has demonstrated that when incolulated orally and intranasally into mice, recombinant S. gordonii strains can colonize for long periods of time, 8–12 weeks, and result in the induction of a vigorous local and systemic immune response. Therefore, two groups of 10 mice were treated with streptomycin to suppress their pre-existing endogenous bacterial flora. Individual mice in each group then received $10^9$ colony forming units of either GP204 or SP204(1-1), both of which are streptomycin resistant, in each of two oronasal implantations (48 hours apart). The level and duration of colonization by the introduced inocula was then monitored by periodic swabbing of the oral cavity and plating on blood agar plates containing streptomycin and/or FUdR. Surprisingly, there was no difference in the number of mice colonized or the average duration of colonization (FIG. 5). In both cases, 100% of the mice were colonized initially.

Although the duration of colonization of individual animals varied between 1–12 weeks, there were no statistically significant differences noted between the GP204 and SP204 (1-1) groups. In contrast, visual inspection of the data suggests that, if anything, on average the SP20(1-1) tended to colonize slightly better than did the GP204. Likewise, enumeration of the extent of colonization showed no demonstrable differences.

DISCUSSION

The results presented here have confirmed an apparent commonality in nucleotide metabolism (at least in the case of thymidine) between gram-negative bacteria, such as *E. coli,* and the gram positive commensal bacterium *S. gordonii.* The data presented here have shown that, when grown in the presence of inhibitory concentrations of FUdR, *S. gordonii* produces FUdR-resistant mutants with a frequency of about $1 \times 10^{-6}$. Identification of the genomic locus responsible for the acquisition of FUdR$^r$ revealed that three independent mutations (SP204(1-1), SP204(1-2), SP204(10-1)) all mapped to the same gene, tdk, which encodes the nucleoside salvage enzyme thymidine kinase. Each of the three FUdR$^r$ mutants acquired a thymidine kinase-deficient phenotype by virtue of the introduction of a nonsense mutation within the tdk open reading frame to produce truncated proteins lacking one or more motifs known to be essential for other thymidine kinase enzymes. Enzyme assays confirmed that none of the truncated enzymes encoded by the SP204(1-1), SP204(1-2), SP204(10-1) tdk genes retained any enzymatic activity.

The original impetus for attempting to isolate FUdR$^r$ *S. gordonii* mutants was to enable this marker to used for the in vitro selection for recombinant candidate vaccine strains and to facilitate the detection of implanted organisms in recipient animals in vivo. Therefore, it was of interest to note that selection conditions could be established (1 µg/ml FUdR, 12.5 µg/ml uridine and 2 µg/ml thymidine) which allowed the growth of FUdR$^r$ mutants while inhibiting the growth of wild-type *S. gordonii,* indicating FUdR$^r$ can be used as a non-antibiotic selection scheme in vitro. It was also shown that the growth of FUdR$^r$ *S. gordonii* (relative to wild-type *S. gordonii*) was not compromised in rich media, indicating that recombinants derived in this manner can be easily grown to high density for use as vaccine inocula. Most importantly, in vivo implantation experiments suggested that the ability of *S. gordonii* to establish colonization and persist in the oral cavity of the mouse is not compromised by the presence of the FUdR$^r$ mutation. This finding suggests that a functional thymidine kinase is not essential in the environment and surrounding milieu found on the murine oral mucosal membranes. Accordingly, this should hold true for commensal bacteria colonizing other mucosal niches, e.g., the intestinal or urogenital tracts, and other species. Taken together, the results obtained here indicate that FUdR$^r$ is useful have utility as a selection scheme and phenotypic marker in *S. gordonii*-based recombinant vaccines. This approach has several potential advantages. First, since FUdR is not routinely used to treat any human diseases there should not be a significant reservoir of FUdR$^r$ oral bacteria to complicate detection of implanted vaccines. This is important factor for enabling the level and duration of vaccine colonization to be monitored during clinical trials. If the $1 \times 10^{-6}$ spontaneous mutation rate proves to be a problem, then FUdR$^r$ can be combined with the naturally occurring streptomycin resistance marker in recombinant vaccines. The odds of a spontaneous FUdR$^r$/Sm$^r$ mutant arising during the course of a clinical trail is vanishingly small. Secondly, the gene encoding FUdR$^r$, thymidine kinase, has been well-studied. Both positive and negative biochemical selection schemes exist for the TK$^-$ phenotype. Furthermore, this phenotype has been used without problem in a large number of prototype viral vaccines. Finally, and most importantly, FUdR is not an antibiotic and FUdR$^r$ is not plasmid-borne. Due to the increasing incidence of antibiotic-resistant pathogenic bacteria, it is essential that if live bacterial strains are to be used as vaccine vectors that they do not contain any engineered, or selected, resistance markers to drugs of clinical relevance in a configuration (such as a plasmid) whereby they could be passed from the implanted commensal to an indigenous pathogen. The FUdR$^r$ genomic marker satisfies both of these criteria.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for isolating a strain of *Streptococcus gordonii* resistant to 5-fluorodeoxyuridine ("FUdR") comprising culturing *S. gordonii* on culture medium containing FUdR; and selecting those *S. gordonii* that grow in the presence of FUdR.

2. The method of claim 1, wherein the culture medium is selected from the group consisting of brain-heart infusion and tryptic soy broth.

3. The method of claim 1, wherein the culture medium comprises 0.5 to 50 µg/ml FUdR.

4. The method of claim 3, wherein the culture medium comprises 1–10 µg/ml FUdR.

5. The method of claim 4, wherein the culture medium further comprises 12.5 µg/ml uridine and 2 µg/ml thymidine.

6. The method of claim 1, wherein the bacteria are not resistant to antibiotics.

7. A *S. gordonii* bacterium isolated by the method of claim 1.

8. An isolated *S. gordonii* bacterium resistant to 5-fluorodeoxyuridine, wherein said bacterium contains a point mutation in the tdk gene that results in the introduction of a translational termination codon in the tdk ORF.

9. A bacterium according to claim 8, wherein said mutation results in the expression of a prematurely terminated TK polypeptide.

10. A bacterium according to claim 9, wherein said prematurely terminated TK polypeptide lacks domain VII.

11. A composition comprising a *S. gordonii* bacterium resistant to fluorodeoxyuridine and a carrier therefor, wherein said bacterium contains a point mutation in the tdk gene that results in the introduction of a translational termination codon in the tdk ORF.

12. A composition according to claim 11, wherein said mutation results in the expression of a prematurely terminated TK polypeptide.

13. A composition according to claim 12, wherein said prematurely terminated TK polypeptide lacks domain VII.

* * * * *